United States Patent [19]

Kaplan et al.

[11] 4,034,089
[45] July 5, 1977

[54] AQUEOUS SUSPENSIONS OF 7[D-α-AMINO-α-(p-HYDROXYPHENYL)-ACETAMIDO]-3-(1,2,3-TRIAZOL-5-YLTHIOMETHYL)-3-CEPHEM-4-CARBOXYLIC ACID 1,2-PROPYLENE GLYCOLATE

[75] Inventors: Murray Arthur Kaplan, Syracuse; Alphonse Peter Granatek, Baldwinsville, both of N.Y.

[73] Assignee: Bristol-Myers Company, New York, N.Y.

[22] Filed: Mar. 5, 1976

[21] Appl. No.: 664,218

Related U.S. Application Data

[60] Division of Ser. No. 534,114, Dec. 18, 1974, Pat. No. 3,970,651, which is a continuation-in-part of Ser. No. 431,251, Jan. 7, 1974, abandoned.

[52] U.S. Cl. .......................... 424/246; 260/243 C
[51] Int. Cl.² ...................................... A61K 31/545
[58] Field of Search ................ 260/243 C; 424/246

[56] References Cited

UNITED STATES PATENTS 3,867,380  2/1975  Dunn et al. ................ 260/243 C

OTHER PUBLICATIONS

The Merck Index Eighth Edition pp. 876–877(1968).

*Primary Examiner*—Nicholas S. Rizzo
*Attorney, Agent, or Firm*—David M. Morse

[57] ABSTRACT

The antibacterial agent 7-[D-α-amino-α-(p-hydroxyphenyl)acetamido]-3-(1,2,3-triazol-5-ylthiomethyl)-3-cephem-4-carboxylic acid, which is a zwitterion, is both purified and converted to a form highly suitable for use in aqueous suspensions by converting it to the crystalline 7-[D-α-amino-α-(p-hydroxyphenyl)acetamido]-3-(1,2,3-triazol-5-ylthiomethyl)-3-cephem-4-carboxylic acid 1,2-propylene glycolate, said propylene glycolate containing 1.0 – 1.6 moles of 1,2-propylene glycol per mole of cephalosporin zwitterion.

6 Claims, No Drawings

AQUEOUS SUSPENSIONS OF 7-[D-αAMINO-α(p-HYDROXYPHENYL)-ACETAMIDO]-3-(1,2,3-TRIAZOL-5-YLTHIOMETHYL)-3-CEPHEM-4-CARBOXYLIC ACID 1,2-PROPYLENE GLYCOLATE

CROSS-REFERENCE TO RELATED APPLICATION

This is a divisional application of co-pending application U.S. Ser. No. 534,114 filed Dec. 18, 1974 now Pat. No. 3,970,651 which in turn is a continuation-in-part of application Ser. No. 431,251 filed Jan. 7, 1974, now abandonded.

BACKGROUND OF THE INVENTION

1. Field of the invention.

The crystalline cephalosporin derivative of the present invention possesses in general the usual attributes of that family of antibacterial agents and is particularly useful in the treatment of bacterial infections by both oral and parenteral administration.

2. Description of the prior art.

The literature concerning this class of antibacterial agents has been reviewed frequently; two recent reviews are The Cephalosporins Microbilogical, Chemical and Pharmacological Properties and Use in Chemotherapy of Infection, L. Weinstein and K. Kaplan, Annals of Internal Medicine, 72, 729–739 (1970) and Structure Activity Relationships Among Semisynthetic Cephalosporins, M. L. Sassiver and A. Lewis, Advances in Applied Microbiology, edited by D. Perlman, 13, 163–236 (1970), Academic Press, New York. Additional reviews which pay particular attention to the patent literature are found in U.S. Pat. Nos. 3,776,907, 3,776,175 and 3,759,904. Solvates, and hydrates in particular, are often encountered in the cephalosporin field, e.g. U.S. Pat. Nos. 3,280,118, 3,502,663, 3,655,656, 3,692,781, 3,708,478 and 3,714,157.

7-[D-α-amino-α-(p-hydroxyphenyl)acetamido]-3-(1,2,3-triazol-5-ylthiomethyl)-3-cephem-4-carboxylic acid is a new cephalosporin, also called BL-S640, which is described and claimed by our colleagues David Willner and Leonard B. Crast, Jr. in U.S. application Ser. No. 318,340 filed Dec. 26, 1972; the entire disclosure of that application is incorporated herein by reference. Application Ser. No. 318,340, disclosed isolation of a 7-[D-α-amino-α-(p-hydroxyphenyl)acetamido]-3-(1,2,3-triazol-5-ylthiomethyl)-3-cephem-4-carboxylic acid methanolate.

SUMMARY OF THE INVENTION

The dual problems confronting applicants were the need for a practical method for purifying 7-[D-α-aminoα-(p-hydroxyphenyl)acetamido]-3 -(1,2,3-triazol-5-ylthiomethyl)-3-cephem-4-carboxylic acid to the high degree necessary for human use and the provision of a form of this drug which could be formulated and administered both orally and parenterally in an aqueous suspension without loss of biological activity and without deleterious changes on standing such as losing crystallinity, not suspending evenly, oiling, clumping, settling out and becoming tacky. These problems were complicated by the fact that in water at alkaline pH, e.g. 7.0 or higher, this compound degrades very rapidly, as by loss of the thiol moiety. In addition, the crude product obtained in chemical production was rather heavily contaminated with residues of the reagents and with various decomposition products from which it could not be separated in reasonable yield by recrystallization or the other usual techniques such as washing with solvents.

Efforts to crystallize the zwitterion or a hydrate thereof failed to give a crystalline product and failed to give substantial purification. No way was found to remove the solvents from solvates in order to obtain essentially anhydrous pure compound and the products so obtained became tacky. The methanolate was undesirable for human use having in mind the known toxicity of that alcohol and in addition its use provide little purification as measured by any increase in biopotency, decrease in color and reduction in content of impurities. An ethanolate was prepared and found to fail to achieve the objectives. Its formation was not accompanied by purification although it was crystalline. In addition, when suspended in water the ethanolate gradually lost its ethanol to change into a solid tacky form which lost crystallinity, did not suspend evenly and gummed in time.

The objectives of the present invention were achieved by the provision according to the present invention of crystalline 7-[D-α-amino-α-(p-hydroxyphenyl)acetamido]-3-(1,2,3-triazol-5-ylthiomethyl)-3-cephem-4-carboxylic acid 1,2-propylene glycolate and as a preferred embodiment crystalline 7-[D-α-amino-α(p-hydroxyphenyl)acetamido]-3-(1,2,3-triazol-5-ylthiomethyl)-3-cephem-4-carboxylic acid 1,2-propylene glycolate having from 1.0 to 1.6 moles of 1,2-propylene glycol per mole of cephalosporin zwitterion and, most particularly, crystalline 7-[D-α-amino-α-(p-hydroxyphenyl)acetamido]-3-(1,2,3-triazol-5-ylthiomethyl)-3-cephem-4 -carboxylic acid mono-propylene glycolate containing 1 mole of 1,2-propylene glycol per mole of cephalosporin zwitterion.

There is also provided by the present invention the process for the preparation of -triazol-7-[D-αamino-α-(p-hydroxyphenyl)acetamido]-3 -(1,2,3-triazol-5 -ylthiomethyl)-3-cephem-4-carboxylic acid 1,2-propylene glycolate; which process comprises adjusting upward the pH of an acidic solution having a pH below about 2.0 of 7-[D-α-amino-α-(p-hydroxphenyl)acetamido]-3-(1,2,3-triazol5-ylthiomethyl)-3-cephem-4-carboxylic acid in aqueous 1,2-propylene glycol by the addition of a base to raise the pH to at least 4.0 and preferably in the range of 4.0 – 5.0 thus precipitating the crystalline propylene gylcolate product which is recovered from the solution by conventional methods such as filtration or centrifugation.

The acidic solution of 7-[D-α-amino-α-(p-hydroxyphenyl)acetamido]-3-(1,2,3-trizol-5-ylthiomethyl)-3-cephem-4-carboxylic acid in the above process may be prepared by adding sufficient acid to an aqueous slurry of the cephalosporin zwitterion or a hydrate or solvate thereof and 1,2-propylene glycol so as to lower the pH of the reaction mixture to below about 2.0, most preferably in the range of about 0.9 to 1.5 and to effect solution of the cephalosporanic acid. The most preferred form of the cephalosporin for use in this process is the methanolate.

The pH of the solution is then raised by addition of sufficient base to effect crystallization of the propylene glycolate product. The most preferred procedure is to slowly add base to a solution having a pH of 1.5 or below to bring the pH to about 1.7 whereupon insoluble impurities precipitate out of solution. The reaction mixture is optionally but preferably carbon-treated and the insoluble products are then separated as by filtration. The acidic solution is adjusted by addition of base to a pH above 4 and preferably in the range of 4.0 to 5.0 at which point the desired product crystallizes from the solution. The product is recovered by conventional procedures, preferably by filtration, and then washed and dried to give the crystalline propylene glycolate having from 1.0 to 1.6 moles of 1,2-propylene glycol per mole of cephalosporin zwitterion.

As illustrated below, the propylene glycolate product of the present invention is crystalline and substantially free of the impurities found in samples of 7-[D-α-amino-α-(p-hydroxyphenyl)acetamido]-3-(1,2, 3 -triazol-5-ylthiomethyl)-3-cephem-4-carboxylic acid made by practical commercial processes. When suspended in water it does not lose biological activity, lose crystallinity, suspend unevenly, oil, clump, settle out or become tacky. As a solid under the usual stringent test conditions it loses no more than ten percent of its bioactivity when stored for one month at b 56° C. At that temperature and also at 100° C. it is far more stable in the solid form than the ethanolate. Either acetone or methanol or ethyl acetate washes can be used to remove excess propylene glycol from the product of the present invention; that is not possible with the other solvates including those containing acetone or ethyl acetate.

In vitro crystalline 7-[D-α-amino-α-(p-hydroxyphenyl)acetamido]-3-(1,2,3-triazol-5-ylthiomethyl)-3-cephem-4-carboxylic acid 1,2-propylene glycolate exhibits the potency and spectrum of activity reported in the above-referenced application Ser. No. 318,340 in a qualitative sense and usually also quantitatively except when it is possible to observe slightly less activity due to its content of the biologically inert propylene glycol. In vivo the results are substantially the same (within the experimental variation inherent in such work) because the product is dosed on a potency basis in terms of the zwitterion as illustrated in the examples.

In the treatment of bacterial infections in man crystalline 7-[D-α-amino-α-(p-hydroxyphenyl)acetamido]-3-(1,2,3-triazol-5-ylthiomethyl)-3-cephem-4-carboxylic acid 1,2-propylene glycolate is administered either orally or parenterally, as preferred by the physician, in an amount of from about 5 to 200 mgm./kg./day and preferably about 5 to 20 mgm./kg./day in divided dosage, e.g. three to four times a day. It is administered in dosage units containing, for example, 125, 250 or 500 mgm. of active ingredient with suitable physiologically acceptable carriers or excipients. The dosage units are in the form of capsules or tablets containing the solid product for oral use or in the form of liquid preparations such as aqueous suspensions for either oral or parenteral administration.

A preferred embodiment of the present invention is the process for the preparation of cyrstalline 7-[D-α-amino-α-(p-hydroxphenyl)acetamido]-3-(1,2,3-triazol-5-ylthiomethyl)-3-cephem-4-carboxylic acid mono-propylene glycolate, which process comprises 1. providing an aqueous solution of 7-[D-α-aminoα-(p-hydroxyphenyl)acetamido]-3-(1,2,3-triazol-5-ylthiomethyl)-3-cephem-4-carboxylic acid and a water-soluble organic compound containing a ketone functional group;

2. adjusting the pH of the solution to about 4.5;

3. diluting the solution with sufficient water to effect precipitation of insoluble impurities;

4. separating the aqueous solution from the insoluble impurities;

5. adding to the aqueous solution sufficient 1,2-propylene glycol to effect crystallization of the desired mono-propylene glycolate; and 6. recovering the crystalline product.

A most preferred embodiment of the present invention is the process for the preparation of crystalline 7-[D-α-amino-α-(p-hydroxyphenyl)acetamido]-3-(1,2,3-triazol-5-ylthiomethyl)-3-cephem-4-carboxylic acid mono-propylene glycolate; which process comprises 1. providing an acidic aqueous solution of 7-[D-α-amino-α-(p-hydroxyphenyl)acetamido]-3-(1,2,3-triazol-5-ylthiomethyl)-3-cephem-4-carboxylic acid and a water-soluble ketoacid selected from pyruvic acid or levulinic acid, said solution having a pH of about 2.0 or below;

2. adjusting the pH of the solution to about 4.5;

3. diluting the solution with sufficient water to precipitate out insoluble impurities;

4. separating the aqueous solution from the insoluble impurities;

5. adding to the aqueous solution sufficient 1,2-propylene glycol to effect crystallization of the desired mono-propylene glycolate; and 6. recovering the crystalline product.

The crystalline mono-propylene glycolate may be prepared according to the above process by treating an aqueous suspension of 7-[D-α-amino-α-(p-hydroxyphenyl)-acetamido]-3-(1,2,3,-triazol-5-ylthiomethyl)-3-cephem-4-carboxylic acid or a hydrate or solvate thereof, preferably a methanol solvate, with a sufficient amount of a water-soluble organic compound containing a ketone functional group to form an aqueous solution of the cephalosporanic acid. In general any water-soluble organic compound containing a ketone moiety may be employed including such compounds as water-soluble ketones, e.g. acetone; ketoacids, e.g. pyruvic acid, levulinic acid, acetoacetic acid, ketoglutaric acid, or salts of ketoacids; and hydroxy-ketones, e.g. dihydroxy-acetone or fructose. The preferred compounds are water-soluble ketoacids. For reasons of availability and cost, the most preferred ketoacids for use in the process are pyruvic acid and levulinic acid. The cephalosporin starting material may be the zwitterion free acid or a hydrate or solvate thereof but is preferably the methanolate because of the greater rate of dissolution of this derivative.

If a complete solution is not obtained upon addition of the ketone-containing organic compound, the pH may be adjusted by addition of acid or base to effect solution. In the preferred procedure a water-soluble ketoacid is used to lower the pH of the aqueous reaction mixture to about 2.0 or below whereupon the cephalosporanic acid goes into solution. If complete solution is not achieved by use of the ketoacid per se, the reaction mixture may be adjusted as by addition of a mineral acid to maximize solubility. The aqueous solution is then adjusted to a pH of about 4.5 by addition of a suitable acid or base. When the preferred ketoacids are used, the pH of the acid solution is raised to the 4.5 level by addition of base, e.g. NaOH, preferably with rapid stirring.

The solution is then diluted with water to allow any water-insoluble impurities to precipitate out. The amount of dilution is not critical but an approximate 1:1 dilution in this step has been found to result in high purity product.

The temperature of the reaction mixture during the above-mentioned steps is not critical. It is preferred, however, to perform these process steps (especially the pH 4.5 adjustment step and dilution step) at a temperature of room temperature or below, most preferably at a temperature in the range of about 5°-20° C., so as to maximize the amount of insoluble impurities formed in the dilution step.

After the dilution step the solid impurities may be separated by conventional procedures, e.g. filtration, from the aqueous solution which contains the cephalosporanic acid and ketone-containing compound. The precise nature of the product in solution is not known, but is believed to be some type of loosely bound soluble physical complex of the cephalosporin zwitterion and keto compound. In any event the use of the keto compound allows the cephalosporin zwitterion to remain in solution at pH 4.5 while the insoluble impurities (including substantially all of the colored impurities) precipitate out. After removal of any solid impurities the aqueous solution is preferably carbon-treated with activated carbon and filtered prior to the propylene glycol addition step.

The aqueous solution is next treated with sufficient 1,2-propylene glycol to induce crystallization of the mono-propylene glycolate which is then recovered as by filtration, washed and dried.

The mono-propylene glycolate prepared according to the above process is a substantially colorless, high potency, crystalline material with excellent color stability and thermal stability. It is especially advantageous for use in aqueous suspensions since on suspension in water it does not lose biological activity or crystallinity and does not oil, suspend unevenly, clump, settle out or become tacky as was the case with other solvates tested. When proper allowance is made for the biologically inert propylene glycol, the mono-propylene glycolate exhibits substantially the same potency and spectrum in vivo and in vitro as the zwitterion product disclosed in application Ser. No. 318,340.

In the treatment of bacterial infections in man the crystalline mono-propylene glycolate is administered either orally or parenterally, as preferred by the physician, in an amount of from about 5 to 200 mgm./kg./day and preferably about 5 to 20 mgm./kg./day in divided dosage, e.g. three to four times a day. It is administered in dosage units containing, for example, 125, 250 or 500 mgm. of active ingredient with suitable physiologically acceptable carriers or excipients. The dosage units are in the form of capsules or tablets containing the solid product for oral use or in the form of liquid preparations such as aqueous suspensions for either oral or parenteral administration.

The present invention besides providing crystalline 7-[D-α-amino-α-(p-hydroxyphenyl)acetamido]-3-(1,2,3-triazol-5-ylthiomethyl)-3-cephem-4-carboxylic acid 1,2-propylene glycolate for use in pharmaceutical formulations also provides methods for purifying 7-[D-α-amino-α-(p-hydroxyphenyl)acetamido]-3-(1,2,3-triazol-5-ylthiomethyl)-3-cephem-4-carboxylic acid which, as mentioned above, is unable to be purified in reasonable yield by normal purification techniques. If in the processes described above impure 7-[D-α-(p-hydroxyphenyl)-acetamido]-3(1,2,3-triazol-5-ylthiomethyl)-3-cephem-4-carboxylic acid is used, the cephalosporin may be recovered in the form of the substantially pure crystalline 1,2-propylene glycolate, said propylene glycolate having from 1.0 – 1.6 moles of 1,2-propylene glycol per mole of cephalosporin zwitterion and, most preferably, 1.0 mole of 1,2-propylene glycol per mole of cephalosporin zwitterion. Substitution of methanol in the procedures described above for the 1,2-propylene glycol used therein produces a crystalline mono-methanolate which may be used as a starting material in the preparation of the crystalline propylene glycolate product of the present invention.

There is also provided by the present invention a stable aqueous suspension useful for the treatment of bacterial infections in mammals comprising at least 30 mgm./ml., and preferably at least 125 mgm./ml. of crystalline 7-[D-α-(p-hydroxyphenyl)acetamido]-3-(1,2,3-triazol-5-ylthiomethyl)-3-cephem-4-carboxylic acid 1,2-propylene glycolate, said propylene glycolate preferably containing 1.0 – 1.6 moles of 1,2-propylene glycol per mole of cephalosporin zwitterion and most preferably 1.0 mole of 1,2-propylene glycol per mole of cephalosporin zwitterion, and having a pH in the range of 2.8 – 5 and preferably in the range of 2.8 – 3.5.

Bioassays

Bioassays were turbidometric against *S. aureus* 209P (A.T.C.C. 6538P) using as the standard a sample of 7-[D-α-amino-α-(p-hydroxyphenyl)acetamido]-3-(1,2,3-triazol-5-ylthiomethyl)-3-cephem-4-carboxylic acid 1,2-propylene glycolate with an assigned potency of 820 mcg./mgm.; the sample contained by chemical analysis 16.7% 1,2-propylene glycol and 0.3% water. The anhydrous zwitterion 7-[D-α-amino-α-(p-hydroxyphenyl)acetamido]-3-(1,2,3-triazol-5-ylthiomethyl)-3-cephem-4-carboxylic acid was assigned a potency of 1000 mcg./mgm. and thus a sample containing 16.7% 1,2-propylene glycol and no other impurities at all (including no water and no excess or unbound 1,2-propylene glycol) would have a calculated potency of 833 mcg./mgm. Calculated percentage contents of 1,2-propylene glycol are 14.1% for 1.0 mole and 20.8% for 1.6 mole of the glycol per mole of zwitterion. The molecular weight of the zwitterion is 462.38.

IR and NMR spectra were run on the same standard sample and the functional group data from the spectra are summarized as follows:

| IR (KBr) | |
|---|---|
| 2400–3600 cm$^{-1}$ | (broad overlapping peaks)-amide NH $NH_3^+$, OH |
| 1780 | β-lactam C=O |
| 1700 | amide C=O |
| 1570 | COO$^-$ |
| 1515 | aromatic C=C |
| NMR (DMSO,dil. DCl) | |
| 7.96 ppm δ | singlet 1H, H$_a$ |
| 6.7 – 7.6 | multiplet, 4H, H$_b$ |
| 5.7 | doublet, 1H, H$_c$ |
| 4.9 – 5.2 | multiplet, 2H, H$_d$, H$_e$ |
| 3.2 – 4.2 | multiplet, 8H*, H$_f$, H$_g$, H$_j$, H$_k$ |
| 1.1 | doublet, 4H*, H$_n$ |

*The integral values indicate 1.33 moles of propylene glycol per mole of BL-S640 zwitterion (18.3% by weight-uncorrected for moisture).

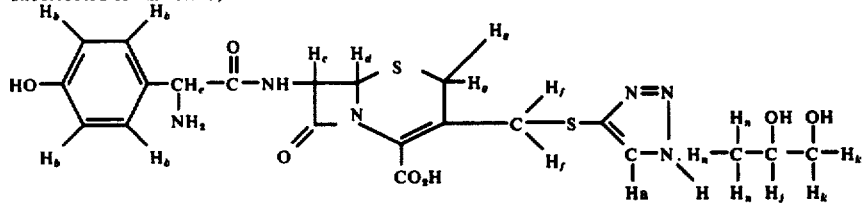

A sample of the 7-[D-α-amino-α-(p-hydroxyphenyl)acetamido]-3-(1,2,3-triazol-5-ylthiomethyl)-3-cephem-4-carboxylic acid mono-propylene glycolate as prepared according to the method of Example 5 was found to have a calculated potency of 865 mcg./mg.; the sample contained by chemical analysis 15.6% 1,2-propylene glycol and 0.3% water.

IR and NMR spectra were run on the same sample of the mono-propylene glycolate and the functional group data from the spectra are summarized as follows:

| IR (KBr) | |
|---|---|
| 2400–3600 cm$^{-1}$ | (broad overlapping peaks)-amide NH, NH$_3^+$, OH |
| 1780 | β-lactam C=O |
| 1705 | amide C=O |
| 1570 | COO$^-$ |
| 1515 | aromatic C=C |
| NMR (DMSO, dilute DCl) | |
| 7.98 ppm δ | singlet, 1H, H$_a$ |
| 6.7–7.6 | multiplet, 4H, H$_b$ |
| 5.68 | doublet, 1H, H$_c$ |
| 4.9–5.2 | multiplet, 2H, H$_d$, H$_e$ |
| 3.2–4.2 | multiplet, 7H, H$_f$, H$_g$, H$_j$, H$_k$ |
| 1.1 | doublet, 3H, H$_h$ |

The integral values indicate 1 mole of propylene glycol per mole of BL-S640 zwitterion.

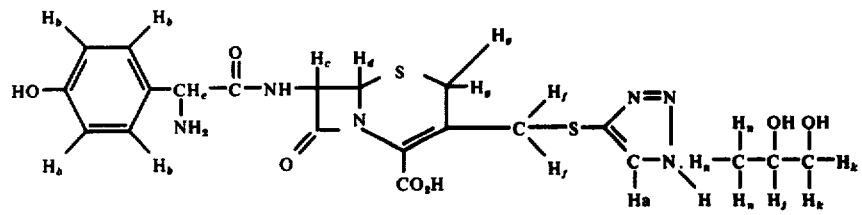

STARTING MATERIALS

D-(−)-2-(p-hydroxyphenyl)glycyl chloride hydrochloride was prepared in a high state of purity and very efficiently by the following procedure.

10.0 g. (about 0.06 moles) of D-(−)-2-(p-hydroxyphenyl)glycine (U.S. Pat. No. 3,489,752) was slurried in 100 ml. of dioxane. The slurry was stirred and COCl$_2$ (phosgene) was passed in while the slurry temperature was held at 50°–58° C. The COCl$_2$ was passed in for a total time of 3.5 hours. A yellow solution was obtained. The solution was purged with nitrogen to expel the excess COCl$_2$. HCl gas was bubbled through the solution for 2.5 hours. The solution was stirred and a small amount was diluted with some ether to obtain some crystals which were added to the batch as seed. The solution was stirred at 20°–25° C. for 16 hours. The resulting slurry of crystalline D-(−)-2-(p-hydroxyphenyl)glycyl chloride hydrochloride was filtered to collect the product. The filter-cake was washed with dioxane and methylene chloride and then dried in a vacuum desiccator over P$_2$O$_5$. The yield of D-(−)-2-(p-hydroxyphenyl)glycyl chloride hydrochloride was 7.3 g.

IR - excellent.

| Elemental Analysis: | | | | |
|---|---|---|---|---|
| | Cl | C | H | N |
| Theory | 31.93 | 43.14 | 4.09 | 6.37 |
| Found | 31.96 | 42.46 | 4.22 | 6.56 |

Acid Chloride Assay:
Acid Chloride - 98.6%
Free COOH - None
Free HCl - None

D-α-t-Butoxycarbonylamino-α-(p-hydroxyphenyl)acetic acid O and

In a three necked flask equipped with a reflux condenser, overhead stirrer and thermometer, there was placed a well-mixed mixture of 8.36 g. (0.05 mole) of D-(−)-p-hydroxyphenylglycine and 3.02 g. (0.075 mole) of magnesium oxide in 120 ml. of 50% aqueous dioxane. The mixture was stirred for 1 hour and then treated with 10.74 g. (0.075 mole) of t-butoxycarbonylazide. The mixture was then stirred and heated at 45°–50° for 17 hours under N$_2$. The solution was diluted with 400 ml. of H$_2$O and extracted twice with 300 ml. of ethyl acetate. The aqueous phase was acidified with 10% citric acid solution to pH 4 and saturated with NaCl. The aqueous mixture was extracted with 3 × 400 ml. of ethyl acetate. The solution was dried over Na$_2$SO$_4$ and the solvent evaporated. The residue was triturated with Skellysolve B to yield D-α-t-butoxycarbonylamino-2-(p-hydroxyphenyl)-acetic acid as a solid weighing 10.4 g. (78.5%).

7-[D-α-t-Butoxycarbonylamino-α-(p-hydroxyphenyl)acetamido]-3-(1,2,3-triazol-5-ylthiomethyl)-3-cephem-4-carboxylic acid To a suspension of 7-amino-3-(1,2,3-triazol-5-ylthiomethyl)-3-cephem-4-carboxylic acid (6.0 g., 19.0 mmole) in 100 ml. dry methylene chloride there was added 8.5 ml. of 1,1,1,3,3,3-hexamethyldisilazane (40.9 mmole). The mixture was stirred and heated at reflux for 4 hours at which time a clear solution was obtained. The solvent was evaporated and the residual oil was subjected to high-vacuum overnight at room temperature. The foamy residue was dissolved in 85 ml. of dry THF and cooled to about −15° before introduction into the subsequent reaction mixture.

D-α-Butoxycarbonylamino-α-(4-hydroxyphenyl)acetic acid, (4.4 g., 16.5 mmole) was dissolved in 145 ml. dry THF. The solution was stirred and cooled to −20°. N-methylmorpholine (1.6 g., 16 mmoles) and isobutylchloroformate (2.3 g., 16.8 mmole) were added in succession at such rate that the temperature of the mixture did not rise about −10°. The resulting mixture was then stirred for 20 minutes at −12° to −15°. It was then cooled to −20° and the THF solution of silylated 7-amino-3-(1,2,3-triazol-5-ylthiomethyl)-3-cephem-4-carboxylic acid was added all at once. The temperature rose to about −12°. External cooling was discontinued until the temperature rose to 0°. At this point an ice-water bath was applied and the mixture stirred for three hours at 2°–3°. This was followed by a period of one hour without external cooling, the temperature rising to 20°. A total of 30 ml. methanol was added and the stirring continued for 15 minutes at room temperature. After evaporating the solvents under reduced pressure, the residue was suspended in 300 ml. ethyl acetate. The suspended solid was filtered off, 11.8 g. The ethyl acetate solution was extracted three times with NaHCO$_3$ (5%) solution. The combined sodium bicarbonate extracts were cooled in an ice-bath, layered with ethyl acetate and acidified to a pH of 2.5 with 42.5% H$_3$PO$_4$. The phases were shaken and then separated. The ethyl acetate solution was then dried by passing it through sodium sulfate and then evaporated to about 15–20 ml. This solution was then added dropwise to stirred cyclohexane (∼400 ml.) contained in an Erlenmeyer flask. After stirring for one-half hour the precipitated solid was collected by filtration. The collected solid 7-[D-α-t-butoxycarbonylamino-α-(p-hydroxyphenyl)acetamido]-3-(1,2,3-triazol-5-ylthiomethyl)-3-cepham-4-carboxylic acid was air dried. It weighed 1.75 g.

7-[D-α-t-Butoxycarbonylamino-α-(p-hydroxyphenyl)-acetamido]-3-(1,2,3-triazol-5-ylthiomethyl)-3-cephem-4-carboxylic acid, 3.5 g., was dissolved in 80 ml. HCOOH, 98–100%, and stirred for 2 hours at room temperature. The HCOOH was evaporated under reduced pressure (aspirator bath temperature not above 40°) and finally axeotroped 3 times with 30 ml. of toluene. The solid was dried overnight under high vacuum over P$_2$O$_5$. A total of 3.5 g. of foam was obtained. The foam, 2 g., was stirred with 300 ml. of H$_2$O:CH$_3$OH (8:2). The solvent was filtered from some solid (0.3 g.), charcoaled with 700 mg. of Darko KB, filtered through diatomaceous earth (Celite) and freeze-dried to yield 0.9 g. of crude 7-[D-α-amino-α-(p-hydroxyphenyl)acetamido]-3-(1,2,3-triazol-5-ylthiomethyl)-3-cephem-4-carboxylic acid. To crystallize the following procedure was used. A suspension of 0.2 g. of the crude material in 6 ml. of 99% methanol was heated in a test tube to boiling. Immediately the heating was discontinued and the melt triturated with seeds. The melt solidified to a crystalline mass. In this manner a total of 0.211 g. of 7-[D-α-amino-α-(p-hydroxyphenyl)acetamido]-3-(1,2,3-triazol-5-ylthiomethyl)-3-cephem-4-carboxylic acid was obtained from 0.400 g. of crude material. The material was dried at 56°/0.1 mm over P$_2$O$_5$ for 20 hrs., m.p. >200° dec. IR and NMR are consistent with structure. The NMR indicates also the presence of ⅓ mole of CH$_3$OH.

Anal. Calcd. for C$_{18}$H$_{18}$N$_6$O$_2$·H$_2$O·1/3CH$_3$OH: C, 44.83; H, 4.38; N, 17.10; S, 13.09. Found: C, 43.97; H, 4.36; N, 15.84; S, 6.18.

A total 6.5 g. (11.55 mmole) of 7-[D-α-t-butoxycarbonylamino-α-(p-hydroxyphenyl)acetamido]-3-(1,2,3-triazol-5-ylthiomethyl)-3-cephem-4-carboxylic acid was dissolved in 175 ml. 98–100% formic acid under anhydrous conditions. The mixture was stirred at room temperature for 2.5 hours. Part of the solution, 125 ml., was evaporated under reduced pressure to an amber oil. The oil was then azeotroped 3 times with 70 ml. of toluene under reduced pressure. The residue was suspended in an 80:20 H$_2$O—CH$_3$OH solution (700 ml.) and stirred for 0.5 hour until most of the solid dissolved, then filtered. The filtration was treated with 1.5 g. of (Darko) charcoal for about 20 minutes. The charcoal was filtered off through a Celite pad. The solution was then freeze-dried in 9 separate 100 ml. round bottom flasks. The freeze-dried material weighed 2.415 g. It was recrystallized in batches of 0.200 g. as described above to yield a total of 0.923 g. 7-[D-α-amino-α-(p-hydroxyphenyl)acetamido]-3-(1,2,3-triazol-5-ylthiomethyl)-3-cephem-4-carboxylic acid. NMR was consistent, indicating the presence of a ⅓ mole of CH$_3$OH.

Anal. Calcd. for C$_{18}$H$_{18}$N$_6$O$_5$S$_2$·H$_2$O. ½CH$_3$OH: C, 44.83; H, 4.38; N, 17.10; S, 13.09. Found: C, 45.77, 44.36; H, 4.44, 4.34; N, 16.61, 16.52; S, 13.01, 13.01.

The acylation of 7-amino-3-(1,2,3-triazol-5-ylthiomethyl)-3-cephem-4-carboxylic acid (7-TACA) to BL-S640 has been carried out in methylene chloride with D-(−)-p-hydroxyphenylglycyl chloride hydrochloride. The yield to BL-S640 methanol solvate was about 45% on a biopotency basis. There was about 15% activity in the mother liquor and about 25% insoluble solids which is unreacted 7-TACA and 7-TACA decomposition product with degraded β-lactam.

The process essentially entails silylation with HMDS of 7-TACA in methylene chloride and then acylation with acid chloride·HCl at 0°–5° C. followed by methanol quench. The reaction is then stripped of methylene chloride and the methanol solution is Darco KB treated. The filtrate is vacuum concentrated and then adjusted to pH 4.8 – 5.0 with concentrated NH$_4$OH, seeded and crystallized.

EQUATIONS

-continued

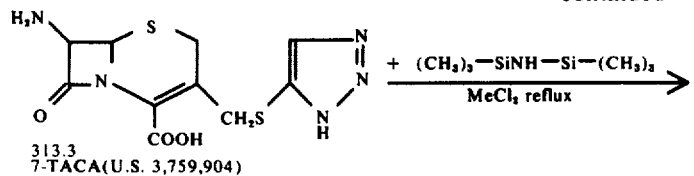

313.3
7-TACA(U.S. 3,759,904)

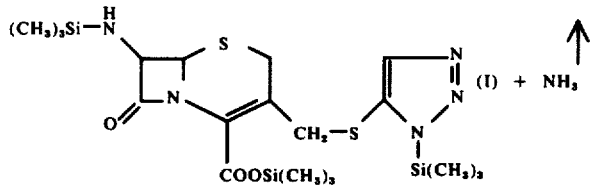

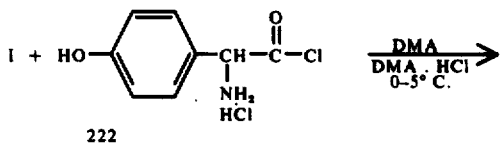

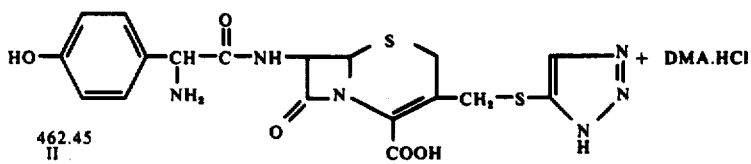

| MATERIALS: (Based on 1.0 kg. of 7-TACA) | | | |
|---|---|---|---|
| Reagent | g | ml. | Moles |
| 7-TACA | 1000.0 | | ~3.20 |
| D-(-)-p-hydroxyphenyl-glycylchloride.HCl | 797.0 | | ~3.60 |
| HMDS (Hexamethyldisilazane) | 965.0 | 1245.0 | ~5.95 |
| DMA.HCl (30% in MeCl₂) | | 320.0 | |
| DMA (Dimethylaniline) | | 480.0 | ~3.78 |
| Methylene chloride (Dry <0.01% KF) | As required | | |
| Methanol (Dry 0.01% KF) | " | | |
| Ammonium hydroxide | " | | |
| "Darco KB" (activated charcoal) | " | | |
| Imidazole | 21.8 | | 0.32 |

PROCEDURE 1. 1000 g. (3.20 moles) of 7-TACA is added to 25 liters of dry methylene chloride (K.F. H₂O <0.01%). The slurry is stirred and 1245 ml. (about 5.95 moles) of HMDS is added to the slurry.

2. The slurry is warmed to reflux and dry nitrogen gas is bubbled through the slurry. The refluxing is continued until complete solution and no settleable solids are noted. Batches of 7-TACA were refluxed for 12-22 hours to obtain a solution that was turbid.

3. After the silylation step is completed, the solution is cooled to about 15°-20° C. and 320 ml. of DMA·HCl (30% in MeCl₂) is added followed by 480 ml. of DMA (dimethylaniline) and 21.8 g. of imidazole. The reaction mix is chilled to 0°-5° C. and 797 g. (3.60 moles) of D-(−)-p-hydroxyphenylglycylchloride·HCl is added in 5 increments over a period of one hour. The slurry is stirred at 0°-5° C. for 10-12 hours or until all the acid chloride goes into solution.

4. The reaction mixture is warmed slowly over 3 hours to 20° C. and held for 2 hours at 20° C. Complete solution of the acid chloride should be noted.

5. 8.3 Liters of dry methanol (KF <0.01%) is added to the solution within one minute with good stirring. The mixture is stirred for 10-15 minutes and then immediately filtered very rapidly to remove insolubles. (In the laboratory, the filtration was carried out on a Buchner funnel and the cake was washed with a wash made up of two parts dry MeCl₂ and one part dry methanol.) This filtration must be done rapidly and the filtration setup prepared before hand so the filtration can be carried out as stated. The filtrate and wash had solids coming out after filtration. It is not known if these solids were product (possible ·HCl salt). It may be that as the reaction with methanol takes place or due to take up of moisture in the laboratory hydrolysis of the silyl ester takes place and product starts to come out. The dark solids filtered out in this step contain some product, 7-TACA and degraded 7-TACA. The wash on the cake scales up to about 10 liters of MeCl₂-MeOH (2-1).

6. The filtrate and wash is vacuum concentrated to remove the MeCl₂ and dry methanol is added as necessary. The solution is concentrated to about 15-18 liters and 600 g. of Darco KB is added. The slurry is stirred for 20-25 minutes and then the slurry is filtered through a diatomaceous earth (Dicalite) precoat and the cake is washed well with 8.0 liters of methanol. This treatment usually gives a yellow-orange filtrate.

7. The filtrate is vacuum concentrated to 12.0 - 13.0 liters and 480 ml. of deionized water is added to the solution. The pH will be in the 2.4 - 3.2 range. The solution is titrated slowly over 30 minutes to pH 4.8 - 5.0 with concentrated ammonium hydroxide. A scaleup of laboratory results would require 420 - 440 ml. of ammonium hydroxide. The solution is seeded when the pH has been adjusted to 4.0. The pH adjustment is carried out at 20° C. after which the slurry is stirred for one hour at 20° C. and then chilled to 0° C. for 16 hours. In the laboratory, after 3 hours stirring in an ice bath the beaker is packed in ice and held in the refrigerator overnight. Crystal growth on the sides of the beaker has always been noted after overnight holding. It is not known at this time if shorter hold time is adequate. However, 3 hours is not adequate from these visual observations. The precipitated product is collected by filtration, washed with MeOH (about filtrate volume) and dried at 45°. The usual yield is 750 – 770 g. of methanol solvate of 7-[D-α-amino-α-(p-hydroxyphenyl)acetamido]-3-(1,2,3-triazol-5-ylthiomethyl)-3-cephem-4-carboxylic acid.

This procedure is an anhydrous one and all precautions are necessary to avoid water contamination or sweating that could cause hydrolysis of the silyl ester and subsequent poor acylation.

The following examples are given in illustration of, but not in limitation of, the present invention. All temperatures are given in degrees Centigrade. Tween 80 is generically known as Polysorbate 80 and is a complex mixture of polyoxyethylene ethers of mixed partial oleic esters of sorbitol anhydrides. The 1,2-propylene glycol used is also known as Propylene Glycol U.S.P. Tetrahydrofuran is abbreviated as THF. Skellysolve B is a petroleum ether fraction of b.p. 60°–68° C. consisting essentially of n-hexane.

DESCRIPTION OF THE PREFERRED EMBODIMENTS

EXAMPLE 1

Preparation of Crystalline
7-[D-α-amino-α-(p-hydroxyphenyl)acetaido]-3-(1,2,3-triazol-5-ylthiomethyl)-3-cephem-4-carboxylic acid Methanolate 1. Fifty grams of 7-[D-α-amino-α-(p-hydroxyphenyl)acetamido]-3-(1,2,3-triazol-5-ylthiomethyl)-3-cephem-4-carboxylic acid is slurried in 250 ml. of 95% V/V methanol/water (95% methanol) solution, at 22°–25° C.
2. Concentrated hydrochloric acid is added with rapid stirring to a pH of 1.3 – 1.5. A solution or near solution is obtained.
3. Adjust the pH to 1.7 with triethylamine.
4. Add 7.5 grams of activated characoal (Darco G-60) and slurry for 0.5 hours.
5. The carbon is removed by filtration and washed with 75 ml. of methanol which is added to the filtrate. Steps 2, 3 and 4 should be completed within 5 hours.
6. The combined wash and filtrate of Step 5 is rapidly stirred. Triethylamine is added over a 5 minute period to pH 4.5. Crystallization starts in about 1–3 minutes. The mixture is slurried for one hour.
7. The crystals are collected by filtration, washed with 100 ml. of methanol and vacuum dried at 56° C. - 24 hours. Bio yield 75–90%; bio-assay = 850–900 mcg./mg.; NMR-IR = Consistent for 1 mole of methanol; % $H_2O$, KF = 2–4.0.

Preparation of Crystalline BL-S640 1,2-Propylene Glycolate

1. Twenty-five grams of the 7-[D-α-amino-α-(p-hydroxyphenyl)acetamido]-3-(1,2,3-triazol-5-ylthiomethyl)-3-cephem-4-carboxylic acid methanolate prepared above is slurried in 150–200 ml. of 75% V/V propylene glycol-water solution at 20°–25° C.
2. Concentrated hydrochloric acid is added to a pH of 1–1.2 to obtain a solution or near solution.
3. Triethylamine (TEA) is slowly added with rapid stirring to obtain a pH of 1.7 - 1.8.
4. Five grams of Darco G-60 is added and the mixture is slurried for 0.5 hour. The carbon is removed by filtration (filtration is slow, an 18.5 cm. SS No. 576 paper is suggested). The carbon filter cake is washed with 40 ml. of 75% V/V propylene glycol water solution. The wash is added to the filtrate.

Steps 2, 3 and 4 above should be completed within 5 hours.

5. Triethylamine is added to pH 4.5 over a 10 minute period to the rapidly stirring filtrate - wash mixture of Step 4. Crystals form in about 1–3 minutes. The mixture is slurried for one hour.
6. The crystals of the 7-[D-α-amino-α-(p-hydroxyphenyl)acetamido]-3-(1,2,3-triazol-5-ylthiomethyl)-3-cephem-4-carboxylic acid propylene glycolate are collected by filtration. Filtration is slow (a 12.5 – 15.0 cm. SS No. 604 paper is suggested). The crystals are washed consecutively with 50 ml. of 75% propylene glycol, 50 ml. of methanol, 50 ml. of acetone and vacuum dried at 56° C. for 24 hours. Biological yield: 80–95%.

Properties of
7-[D-α-amino-α-(p-hydroxyphenyl)acetamido]-3-(1,2,3-triazol-5-ylthiomethyl)-3-cephem-4-carboxylic acid propylene glycolate.

a. Bio-assay = 750–790 mcg./mg.
b. IR-NMR = Consistent for a structure containing 1.3 – 1.5 MOLES of propylene glycol (17–19% propylene glycol). No loss of the 3-triazole side chain evident.
c. % Water, K.F. = 1–3.0.
d. Crystal morphology = 100% crystalline microcrystals, triangular shaped.
e. M.P. = 182°–184° C. (D, hot stage).
f. $[\alpha]_d^{25}$ (C = 1%; 1N-HCl) = +53°.
g. Water solubility = Approximately 10 mg./ml. in water at 23° C.
h. Loss of bioactivity on storage at elevated temperatures: 100° C., 24 hours = <6%; 48 hours = <12%; 56° C., 1 month = <10%.

EXAMPLE 2

| MATERIALS | Wt.,g. | Vol.,ml. | Moles |
|---|---|---|---|
| 7-[D-α-Amino-α-(p-hydroxyphenyl)acetamido]-3-(1,2,3-triazol-5-ylthiomethyl)-3-cephem-4-carboxylic acid methanolate (Note 1) | 1,000 | | 2.02 |
| 6N HCl | | 425–460 | |
| Triethylamine | | ~330 | |
| Carbon | 50 | | |
| Propylene glycol (1,2-propanediol) | | 5,650 | |
| Ethyl acetate | | 3,400 | |
| Methylene chloride | | 800 | |

PROCEDURE

1. Charge a suitable vessel equipped for stirring and pH control with 1.5 liters of propylene glycol and 1.5 liters of deionized water.
2. Add 1000 g. of 7-[D-α-amino-α-(p-hydroxphenyl)acetamido]-3-(1,2,3-triazol-5-ylthiomethyl)-3-cephem-4-carboxylic acid methanolate into the above propylene glycol - water mixture (1:1).

3. Under good agitation, acidify the slurry with about 425 ml. of 6 N HCl to pH 0.9 - 1.3 over 15 minutes at 25° C. A dark, clear solution should be obtained.

4. Immediately adjust the solution to pH 1.4 - 1.7 with triethylamine (TEA). It only takes 20–30 ml. A small amount of white solid is precipitated out. The precipitate is presumed to be p-hydroxyphenyl glycine or a derivative thereof.

5. Treat the solution with 50 g. of Darco KB. Agitate the slurry at 25° C. for 15 minutes.

6. Remove the carbon by filtering through a precoated diatomaceous earth (Dicalite) filter. The filtration area is 1.3 cm² per g. Lab filtrations used vacuum, were slow and required frequent scraping of the cake surface. Pressure filtration is expected to help this slow rate of filtration. The carbon cake is washed with 1400 ml. of 7:3 propylene glycol:water. Hold this wash separate.

7. Pass the filtrate of Step 6 through a suitable sterile filter into a sterile container. The filtration area is 1.3 cm² per g. Wash the filter pad with the wash of Step 6 and again wash with 1000 ml. of sterile propylene glycol - water mixture (7:3).

8. Add 1.75 l of sterile propylene glycol into the sterile solution of Step 7.

9. Under vigorous agitation, slowly adjust the solution of Step 8 to pH 4.1–4.3 with about 300 ml. of sterile TEA over a period of 20 to 30 minutes.

10. Continuously stir the slurry at 25° C. for 4 to 5 hours. The slurry is stable to overnight storage.

11. Filter the sterile crystals and wash the cake with 1000 ml. of sterile propylene glycol - water (7:3) and then 1000 ml. of sterile ethyl acetate.

12. Reslurry the sterile crystals in 2000 ml. of sterile ethyl acetate to remove the excess propylene glycol.

13. Collect the solid by filtration and further wash the cake with 1.2 liters of sterile ethyl acetate - methylene chloride mixture (1:2)

14. Dry the product in 50° C. vacuum oven for 15 hours. The yield is about 820 - 910 gm. of crystalline 7-[D-α-amino-α-(p-hyddroxyphenyl)acetamido]-3-(1,2,3-triazol-5-ylthiomethyl)-3-cephem-4-carboxylic acid 1,2-propylene glycolate.

15. Analyses of Product: Propylene glycol: 1.2 - 1.3 moles per mole of 7-[D-α-amino-α-(p-hydroxyphenyl)acetamido]-3-(1,2,3-triazol-5-ylthiomethyl)-3-cephem-4-carboxylic acid by NMR. Pyridine: less than 0.04% by VPC. Bio-assay: 800–850 mcg./mg.

NOTES

1. The primary BL-S640 methanolate contains 0.4 to 0.6% pyridine.

2. The white precipitate at Step 4 could be prefiltered through a coarse sintered glass filter with diatomaceous earth (Dicalite). The following carbon filtration is easier.

3. If a dark colored 7-[D-α-amino-α-(p-hydroxyphenyl)acetamido]-3-(1,2,3-triazol-5-ylthiomethyl)-3-cephem-4-carboxylic acid methanolate is used, a higher percent carbon treatment may be required. More difficulty is then expected in the filtration.

4. Step 6 and Step 7 should be completed as soon as possible. The sterile filtrate should not be stored longer than 5 hours. If necessary, part of sterile TEA could be added into the filtrate before the washing operation is done.

5. The sterile propylene glycol of Step 8 is sterilized preferably by heating to 80° C. for 30 minutes followed by sterile filtration. Cool to 25° C. before adding into sterile 7-[D-α-amino-α-(p-hydroxyphenyl)acetamido]-3-(1,2,3-triazol-5-ylthiomethyl)-3-cephem-4-carboxylic acid solution. Alternatively, the sterile propylene glycol could be in the receiver of the Step 7 sterile filtration.

EXAMPLE 3

Preparation of Sterile Crystalline Parenteral Grade 7-[D-α-amino-α-(p-hydroxyphenyl)acetamido]-3-(1,2,3-triazol-5-ylthiomethyl)-3-cephem-4-carboxylic acid Propylene Glycolate 1. Twenty-five grams of 7-[D-α-amino-α-(p-hydroxyphenyl)acetamido]-3-(1,2,3-triazol-5-ylthiomethyl)-3-cephem-4-carboxylic acid methanolate or recrystalized 7-[D-α-amino-α-(p-hydroxyphenyl)acetamido]-3-(1,2,3-triazol-5-ylthiomethyl)-3-cephem-4-carboxylic acid propylene glycolate is slurried in 150–200 ml. of 75% V/V propylene glycol-water solution at 20°–25° C.

2. Concentrated hydrochloric acid is added to a pH of 1–1.2 to obtain a solution or near solution.

3. Triethylamine (TEA) is slowly added with rapid stirring to obtain a pH of 1.6–1.8.

4. Five grams of Darco G-60 is added and the mixture is slurried for 0.5 hour. The carbon is removed by filtration (filtration is slow, an 18.5 cm. SS No. 576 paper is suggested). The carbon filter cake is washed with 40 ml. of 75% V/V propylene glycol water solution. The wash is added to the filtrate.

5. Pass the combined filtrate and wash of Step 4 through a sterile 0.22 micron Millipore filter into an appropriate sterile container or tank located in a sterile area.

Steps 2, 3, 4 and 5 above should be completed within 6 hours.

6. Sterile triethylamine is added to pH 4.5 over a 10 minute period to the rapidly stirring sterile solution of Step 5. Crystals form in about 1–3 minutes. The mixture is slurried for one hour.

7. The sterile crystals are collected by sterile filtration. Filtration is slow (a 12.5 - 15.0 cm. SS No. 604 paper is suggested). The crystals are washed with 50 ml. of sterile 75% propylene glycol, 50 ml. of sterile methanol, 50 ml. of sterile acetone and vacuum dried at 56° C. for 24 hours. Biological yield: 80–95%.

8. The sterile crystals may be sterilely micropulverized to 200 mesh or sterilely micronized.

Properties of 7-[D-α-amino-α-(p-hydroxyphenyl)acetamido]-3-(1,2,3-triazol-5-ylthiomethyl)-3-cephem-4-carboxylic acid propylene glycolate a. Bio-assay = 800–860 mcg./mg.

b. IR-NMR = Consistent for a structure containing 1.3 - 1.5 moles of propylene glycol (17–19% propylene glycol). No loss of the 3-triazole side chain evident.

c. % Water, K.F. = 1–3.0.

d. Crystal morphology = 100% crystalline Microcrystals, triangular shaped e. M.P. = 182°–184° C. (D, hot stage)

f. $[\alpha]_D^{25}$ (C = 1%; 1N-HCl) = +53° g. Water solubility = Approximately 10 mg./ml. in water at 23° C.

h. Heat stability: 100° C., 24 hours = <6% loss; 100° C., 48 hours = <12% loss; 56° C., 1 month = <10% loss of bioactivity.

EXAMPLE 4

Preparation Of Purified BL-S640 Mono-Methanolate

1. One hundred grams of BL-S640 methanolate or 1,2-propylene glycolate is rapidly stirred in 300 ml. of water.
2. Eighty grams of levulinic acid is added.
3. Concentrated hydrochloric acid is slowly added with rapid stirring to pH 0.8 – 1.2 to obtain a solution or near solution. The solution is cooled to 20°–25° C. if required.
4. Forty percent sodium hydroxide is added over a five minute period to the very rapidly stirring solution of step (3) to a pH of 4.5 (a precipitate may come down at pH 2.0 – 3.0 and then go into solution at pH 4 – 4.5). Do not allow the temperature to rise above 27° C.
5. The solution or near solution is cooled to 4°–10° C. and added with very rapid stirring to 500 ml. of 4°–10° C. water. A precipitate forms.
6. The mixture is stirred at 4° – 10° C. for five minutes. The precipitate (X) which contains most of the color and impurities including des-triazole BL-S640 is removed by filtration. The precipitate is washed with 50 ml. of water (do not add the wash water to the filtrate of solid X), 75 ml. of methanol (do not add the methanol to the filtrate of solid X) and vacuum-dried at 50° C. for 25 hours. Yield 5–15 grams of tan-brown solids. (0–500 units/mg.)
7. Fifteen grams of Darco G60 or KB activated carbon is added to the filtrate of precipitate (X), step 6. The mixture is stirred at ambient temperature for 0.5 hours.
8. The carbon is removed by filtration and washed with 40 ml. of water. The water wash is added to the filtrate.
9. The filtrate is sterilely filtered through a 0.22 micron Millipore filter. Steps 4–9 should be completed within four hours.
10. An equal volume (approximately one liter) of sterile, pyrogen-free methanol is added to the pH 4.5 solution of step 9 with moderate stirring. Crystals form in about one minute. Maintain pH at 4.5.
11. The mixture is stirred at 18°–23° C. for one hour.
12. The brilliant white crystals are removed by filtration, washed with 175 ml. of sterile 50% methanol, 300 ml. of sterile methanol and vacuum-dried at 56° C. for 24 hours. Yield: 65–75 grams (bio yield; 70–80%).

EXAMPLE 5

Preparation Of BL-S640 Mono-Propylene Glycolate

1. One hundred grams of BL-S640 methanolate or 1,2-propylene glycolate is rapidly stirred in 300 ml. of water.
2. Eighty grams of levulinic acid is added.
3. Concentrated hydrochloric acid is slowly added with rapid stirring to pH 0.8 – 1.2 to obtain a solution or near solution. The solution is cooled to 20°–25° C. if required.
4. Forty percent sodium hydroxide is added over a five minute period to the very rapidly stirring solution of step (3) to a pH of 4.5 (a precipitate may come down at pH 2.0 – 3.0 and then go into solution at pH 4 – 4.5). Do not allow the temperature to rise above 27° C.
5. The solution or near solution is cooled to 4° – 10° C. and added with very rapid stirring to 500 ml. of 4°–10° C. water. A precipitate forms.
6. The mixture is stirred at 5°–10° C. for five minutes. The precipitate (X) which contains most of the color and impurities including des-triazole BL-S640 is removed by filtration. The precipitate is washed with 50 ml. of water (do not add the wash water to the filtrate of solid X), 75 ml. of methanol (do not add the methanol to the filtrate of solid X) and vacuum dried at 50° C. for 25 hours. Yield 5–15 grams of tanbrown solids. (0–500 units/mg.)
7. Fifteen grams of Darco G60 or KB is added to the filtrate of precipitate (X), step 6. The mixture is stirred at ambient temperature for 0.5 hours.
8. The carbon is removed by filtration and washed with 40 ml. of water. The water wash is added to the filtrate.
9. The filtrate is sterilely filtered through a 0.22 micron Millipore filter. Steps 4–9 should be completed within four hours.
10. An equal volume (approximately one liter) of sterile, pyrogen free propylene glycol is added to the pH 4.5 solution of step 9 with moderate stirring. Crystals form in about one minute. Maintain pH at 4.5.
11. The mixture is stirred at 18°–23° C. for one hour.
12. The brilliant white crystals are removed by filtration, washed with 175 ml. of sterile 50% propylene glycol water, 450 ml. of sterile methanol and vacuum dried at 56° C. for 24 hours.
13. Yield 70–80 grams (bio yield 75–85 percent of BL-S640 mono-propylene glycolate.

A sample of the mono-propylene glycolate product obtained according to the method of Example 5 was subjected to analysis with the following results:

a. Bio-assay = 865 mcg./mg.
b. IR-NMR = consistent for a structure containing one mole of propylene glycol per mole of cephalosporin zwitterion.
c. % water, K.F. = 0.3.
d. Crystal morphology = well-defined rod-like crystals.
e. $[\alpha]_D^{23}$ (C= 1%; 1N-HCl) = + 55.9°.
f. % Propylene glycol by chemical analysis = 15.6.
g. Other solvents = 0.1%.
h. UV absorption spectrum (in 0.1 N HCl) : $\lambda_{max}$ = 227 nm (a = 28.4) and $\lambda_{max}$ 272 nm(a = 16.6).

A sample of mono-propylene glycolate was examined by x-ray powder diffraction technique using the procedure described below.

Results

The sample was highly crystalline, yielding 35 measurable diffraction lines. The data in the form of d-spacings and relative itensities are as follows:

| Line | Spacing d (A) | Relative Intensity |
|---|---|---|
| 1 | 10.11 | 65 |
| 2 | 9.26 | 32 |
| 3 | 7.83 | 18 |
| 4 | 7.33 | 51 |
| 5 | 6.88 | 82 |
| 6 | 6.28 | 56 |
| 7 | 5.71 | 42 |
| 8 | 5.27 | 3 |
| 9 | 5.02 | 41 |
| 10 | 4.68 | 62 |

-continued

| Line | Spacing d (A) | Relative Intensity |
|------|---------------|---------------------|
| 11 | 4.46 | 99 |
| 12 | 4.30 | 59 |
| 13 | 4.13 | 35 |
| 14 | 3.91 | 90 |
| 15 | 3.80 | 100 |
| 16 | 3.63 | 37 |
| 17 | 3.47 | 49 |
| 18 | 3.35 | 13 |
| 19 | 3.24 | 11 |
| 20 | 3.13 | 14 |
| 21 | 3.02 | 18 |
| 22 | 2.95 | 17 |
| 23 | 2.85 | 25 |
| 24 | 2.78 | 55 |
| 25 | 2.72 | 23 |
| 26 | 2.61 | 18 |
| 27 | 2.53 | 20 |
| 28 | 2.49 | 6 |
| 29 | 2.35 | 8 |
| 30 | 2.31 | 14 |
| 31 | 2.27 | 14 |
| 32 | 2.24 | 14 |
| 33 | 2.19 | 10 |
| 34 | 2.14 | 14 |
| 35 | 2.10 | 15 |

The details for this determination of x-ray diffraction properties are as follows:

A small amount of sample was sealed in a 0.2 mm. diameter low scattering glass capillary tube which was mounted for exposure in a 114.6 mm. diameter Debye-Scherrer powder diffraction camera. The exposure time was 4 hours on a Norelco X-ray Generator operated at 35 KV-20 mA using a standard focus copper target X-ray tube (weighted $CuK_\alpha$ wavelength $\lambda$ - 1.5418 A). Kodak No-Screen X-Ray Film was used and developed for 3 minutes at 20° C. in Kodak Liquid X-ray Developer.

A very small amount of crystalline sodium fluoride was mixed in with some samples to provide internal calibration. In addition, a sample of pure NaF was run through the complete procedure for the same purpose.

The films were read on a Norelco Debye-Scherrer film reader, recording the positions of the diffraction rings to the nearest 0.05 mm. The data were corrected for film shrinkage and the interplanar spacings (d-spacings) were calculated from the corrected data. A computer program (X-RAY, by P. Zugenmaier) was used for all calculations. The accuracy in the resulting d-spacing data was ~1%.

An intensity record of all films was obtained using a Joyce-Loeble Mark IIIC Recording Microdensitometer (scan ratio 5:1, 0.1 O.D. wedge). Relative intensities on a scale 1-100 were assigned to all recognizable diffraction rings using peak intensities corrected for the background reading.

EXAMPLE 6

Preparation Of Purified BL-S640 Mono-Methanolate

1. One hundred grams of pyruvic acid is dissolved in 250-300 ml. of water.

2. One hundred grams of BL-S640 propylene glycolate or BL-S640 methanolate is sprinkled in with rapid stirring over a five minute interval. A pH 2.0 solution or near solution is obtained.

3. The solution is cooled to 10° C.

4. Forty percent sodium hydroxide is added over a five minute period to the very rapidly stirring solution of step (3) to a pH of 4.5 (a precipitate may come down at pH 2.0 - 3.0 and then go into solution at pH (4 - 4.5). Do not allow the temperature to rise above 27° C.

5. The solution or near solution is cooled to 8°-12° C. and added with very rapid stirring to 500 ml. of 4°-10° C. water. A precipitate forms.

6. The mixture is stirred at 8°-12° C. for three minutes. The precipitate (6X) which contains most of the color and impurities including des-triazole BL-S640 is removed by vacuum filtration. Filtration is slow. Suck the filter cake as dry as possible. Place the filter paper and filter cake in 300 ml. of methanol and hold for four hours. Air dry the filter paper and filtercake, scrape off the solids and vacuum dry at 50° C. for 24 hours. Yield 5-25 grams of tan solids (potency 200-700 units/mg.) Save for reprocessing.

7. Fifteen grams of Darco G60 or KB is added to the filtrate of precipitate (6X) in Step 6. The mixture is stirred at ambient temperature for 0.5 hours.

8. The carbon is removed by filtration and washed with 40 ml. of water. The water wash is added to the filtrate.

9. The filtrate is sterilely filtered through a 0.22 micron Millipore filter. Steps 4-9 should be completed within four hours. The temperature should be below 24° C for Steps 7-9.

10. An equal volume (approximately one liter) of sterile, pyrogen-free methanol is added to the pH 4.5 solution of Step 9 with moderate stirring. Crystals form in about one minute. Maintain pH at 4.5.

11. The mixture is stirred at 10°-20° C. for one hour.

12. The brillant, white crystals are removed by filtration, washed with 175 ml. of sterile 50% methanol water, 450 ml. of sterile methanol and vacuum-dried at 56° C. for 24 hours.

13. Yield 55-60 grams (bio yield 60-75 percent of crystalline BL-S640 mono-methanolate (Bio-assay 930-960 units/mg.

EXAMPLE 7

PREPARATION OF BL-S640 MONO-PROPYLENE GLYCOLATE

1. One hundred grams of pyruvic acid is dissolved in 250-300 ml. of water.

2. One hundred grams of BL-S640 propylene glycolate or BL-S640 methanolate is sprinkled in with rapid stirring over a five minute interval. A pH 2.0 solution or near solution is obtained.

3. The solution is cooled to 10° C.

4. Forty percent sodium hydroxide is added over a five minute period to the very rapidly stirring solution of Step (3) to a pH of 4.5 (a precipitate may come down at pH 2.0 - 3.0 and then go into solution at pH 4 - 4.5). Do not allow the temperature to rise above 27° C.

5. The solution or near solution is cooled to 8°-12° C. and added with very rapid stirring to 500-600 ml of 8°-12° C. water. A precipitate forms.

6. The mixture is stirred at 8°-12° C. for three minutes. The precipitate (6X), which contains most of the color and impurities, including des-triazole BL-S640 is removed by vacuum filtration. Filtration is slow. Suck the filter cake as dry as possible. Place the filter paper and filter cake in 300 ml. of methanol and hold for four hours. Air dry the filter paper and filtercake, scrape off the solids and vacuum dry at 50° C. for 24 hours. Yield 5-25 grams of tan solids (potency 200-700 units/mg.) Save for reprocessing.

7. Fifteen grams of Darco G60 or KB is added to the filtrate of precipitate (6X) in Step 6. The mixture is stirred at ambient temperature for 0.5 hours.

8. The carbon is removed by filtration and washed with 40 ml. of water. The water wash is added to the filtrate.

9. The filtrate is sterilely filtered through a 0.22 micron Millipore filter. Steps 4–9 should be completed within four hours. The temperature should be below 24° C. for Steps 7–9.

10. An equal volume (approximately one liter) of sterile, pyrogen-free propylene glycol is added to the pH 4.5 solution of Step 9 with moderate stirring. Crystals form in about one minute. Maintain pH at 4.5.

11. The mixture is stirred at 10°–20° C. for one hour.

12. The brilliant, white crystals are removed by filtration, washed with 175 ml. of sterile 50 % propylene glycol water, 450 ml. of sterile methanol and vacuum-dried at 56° C. for 24 hours.

13. Yield 55–60 grams (bio yield 60–70 percent of the crystalline BL-S640 mono-propylene glycolate.

lene chloride equal to approximately one-fifth the weight of BL-S640 propylene glycolate required.

5. Using aseptic conditions, the solution of Step 4 is passed, under positive pressure through a sterile 0.22 micron Millipore filter into an appropriate sterile container located in a sterile area.

6. Using the liquid addition apparatus of the blender, add the required volume of sterile, pyrogen-free methylene chloride solution of Step 5 in five equal portions. After each addition of solution the intensification bar is utilized for a maximum of two minutes using 4 agitation periods during the fifteen minutes blending period required for each addition of solution. At the termination of each blending period the pressure developed during the blending process must be released (noted on gauge on shell of blender) and vacuum applied to remove the methylene chloride vapors. This must be repeated to assure complete removal of vapors. To aid in the evaporation and removal of vapors heat to 115° F may be applied to the shell by circulating hot water through the walls.

Example 8

Intramuscular 7-[D-α-amino-α-(p-hydroxyphenyl)acetamido]-3-(1,2,3-triazol-5-ylthiomethyl)-3-cephem-4-carboxylic acid [Herein called BL-S640] Propylene Glycolate (Micronized) (Label claim is 250 mg./ml. BL-S640 Activity as BL-S640 Propylene Glycolate

FORMULA

| | Per 1 Dose | Per 5 Doses | Per 10 Doses | Per 16 Doses |
|---|---|---|---|---|
| Sterile, Micronized 7-[D-α-amino-α-(p-hydroxyphenyl)acetamido]-3-(1,2,3-triazol-5-ylthiomethyl)-3-cephem-4-carboxylic acid Propylene Glycolate | *0.250 Gram of activity | 1.250 Gram of activity | 2.50 Gram of activity | 4.00 Gram of activity |
| Propyl Paraben | 0.0001 Gram | 0.0005 Gram | 0.001 Gram | 0.0016 Gram |
| Methyl Paraben | 0.0009 Gram | 0.0045 Gram | 0.009 Gram | 0.0144 Gram |
| Sodium Chloride (Sterile, Micropulverized) | 0.002 Gram | 0.010 Gram | 0.02 Gram | 0.032 Gram |
| Tween-80 | 0.001 Gram | 0.005 Gram | 0.01 Gram | 0.016 Gram |
| Lecithin | 0.002 Gram | 0.01 Gram | 0.02 Gram | 0.032 Gram |
| Polyvinylpyrrolidone (Povidone) | 0.005 Gram | 0.025 Gram | 0.05 Gram | 0.08 Gram |

*Label claim is 250 mg./ml. BL-S640 activity as the propylene glycolate.
The amount of BL-S640 propylene glycolate required is calculated as follows:

$$\frac{0.250 \text{ grams} \times 1000}{\text{Potency of BL-S640 propylene glycolate in mcg./mg.}} = \text{Weight in grams of BL-S640 propylene glycolate required.}$$

This weight may also be increased in amount by adding increments based on the following factors:
1) Overbatch required for shelf life (stability).
2) Overfill required for vial, syringe and needle holdup.
3) Machine fill variability.

Intramuscular BL-S640 Propylene Glycolate (Micronized) (Label claim is 250 mg./ml. BL-S640 activity as BL-S640 Propylene Glycolate 1. The BL-S640 propylene glycolate to be used must be sterile, pyrogen free and handled aseptically throughout the processing.

2. The BL-S640 propylene glycolate is sterilely micronized in a sterile micronizer.

3. The sterile micronized BL-S640 propylene glycolate plus the sterile sodium chloride is then loaded into a sterile Patterson Kelly V Blender equipped with an intensification bar adapted for liquid addition. The blender has been rendered sterile by spraying with peracetic acid and exposure to ethylene oxide gas for 16 hours prior to use. Care must be taken, before blender is loaded, so that no condensation of the gases has occurred inside the blender. The condensation may be prevented by obtaining proper atmospheric room temperature. The blender is run for 30 minutes with intensification action to assure initial blending of the material.

4. The lecithin, methyl and propyl parabens, Tween-80 and Povidone are dissolved in a volume of methy- 7. When all the solution has been added and blend properly vacated of vapors the material is dropped from the blender and trayed for drying. The material is placed in covered trays and placed in a hot air atmospheric oven and dried for six hours. The temperature of heated air should not exceed 130° F. After six hours of heating, the heat is turned off and air circulated over the trays for 10 hours to assure complete drying.

8. Repulverize the coated material utilizing the procedure of Step 2 so that the following requirement is met:

Retained on a 200 Mesh Screen 0.1% Maximum

9. Collect into sterile containers as a finished bulk product for final disposition.

10. The proper amount of coated BL-S640 propylene glycolate is filled, using aseptic technique, into officially designated size silicone coated vials.

EXAMPLE 9

| Formula of BL-S640 Propylene Glycolate Capsules (250 mg. BL-S640 Activity per Capsule) | Per Capsule |
|---|---|
| BL-S640 Propylene Glycolate | +0.3148 Gm. |
| Lactose U.S.P. | 0.0087 Gm. |
| Magnesium Stearate U.S.P. | 0.0015 Gm. |
| Net fill weight per capsule | 0.3250 Gm. |

+ These combined weights represent 262.5 mg. of activity which is 5% excess over label claim of 250 mg. activity, based on a potency of 834 mcg./mg. for the composite BL-S640 Propylene Glycolate blend. To calculate the amount of BL-S640 Propylene Glycolate to use apply the following formula:

(0.2625 × 1000)/834 = 0.3148 Gm. of blend to use per capsule

NOTE: Each lot of BL-S640 Propylene Glycolate is passed through No. 60 mesh screen prior to blending and mixing with remaining ingredients and filling into No. 1 size capsules.

EXAMPLE 10

BL-S640 Propylene Glycolate for I.M. Suspension, 300 mg.

Formula

| | Per Vial |
|---|---|
| BL-S640 Propylene Glycolate, sterile, micronized | + 0.359 Gm. |
| Sodium Chloride, sterile, micropulverized | 0.0024 Gm. |
| Tween 80 | 0.0012 Gm. |
| Lecithin | 0.0024 Gm. |
| Polyvinylpyrrolidone (Povidone) | 0.0060 Gm. |
| Blend and fill; Total Weight per 10 ml. Vial | 0.3710 Gm. |

+ This weight is equivalent to 300 mg. of BL-S640 activity.

The addition of 9.7 ml. of water for injection results in a suspension having 300 mg. BL-S640 activity per ml.

EXAMPLE 11

BL-S640 Propylene Glycolate for I.M. Suspension, 1.0 Gram

Formula

| | Per Vial |
|---|---|
| BL-S640 Propylene Glycolate, sterile, micronized | + 1.196 Gm. |
| Sodium Chloride, sterile, micropulverized | 0.008 Gm. |
| Tween 80 | 0.004 Gm. |
| Lecithin | 0.008 Gm. |
| Polyvinylpyrrolidone (Povidone) | 0.020 Gm. |
| Bled the above to give | 1.236 Gm. |
| More of the above blend added for VNS holdup++ | 0.349 Gm. |
| Total weight per 5 ml. vial | 1.585 Gm. |

+ This weight is equivalent to 1.0 Gram of BL-S640 activity.
++ VNS refers to the vial, needle and syringe.

The addition of 3.7 ml. of water for injection results in a suspension having 250 mg. BL-S640 activity per ml.

Stabilities on storage were measured for reconstituted 250 mg./ml. of activity BL-S640 propylene glycolate I.M. suspensions prepared as described above with the following results:

| | % Loss of Bioactivity at 23° C. | |
|---|---|---|
| Time in Days | Lot 1 | Lot 2 |
| 1 | | |
| 3 | | |
| 7 | 2.0 | 2.1 |
| 14 | 2.0 | 1.1 |
| 21 | +8.1 | +6.3 |
| 30 | 1.0 | 5.3 |
| 42 | 0.0 | +1.1 |
| 60 | 5.1 | 4.2 |
| 90 | 1.0 | 9.5 |

| | % Loss of Bioactivity at 4° C. | |
|---|---|---|
| Time in Days | Lot 1 | Lot 2 |
| 30 | +1.0 | 1.1 |
| 45 | +1.0 | 1.1 |
| 60 | 3.0 | 2.1 |
| 90 | 1.0 | 5.3 |
| 120 | | |
| 180 | | |

The dry powders are stable for at least 4 months at 56° C.

The suspensions exemplified above are improved by the addition of a small amount of a nontoxic, pharmaceutically acceptable polycarboxylic acid, e.g. citric acid. The amount of acid used (which is, of course, added in dry form to the blend of the other solid ingredients) is that which is sufficient to provide a pH in the range of 2.8 – 3.5 upon reconstitution; without the added acid the formulations have pH's in the range of 4.4 – 5. The improvements consist of better color, that is, less development of undesired color on standing, and also a lower rate of loss of bioactivity on standing.

Oral Bioavailability In Beagle Dogs

Three beagle dogs (mean weight of 8.2 ± 0.4 kg.) were administered 200 mesh 7-[D-$\alpha$-amino-$\alpha$-(p-hydroxyphenyl)-acetamido]-3-(1,2,3-triazol-5-ylthiomethyl)-3-cephem-4-carboxylic acid propylene glycolate (bioassay 820 mcg./mgm.) orally at doses of 30 mg. of activity/kg. in hard gelatin capsules. All doses and concentrations reported herein are in terms of the amphoteric material and were corrected for differences in biopotency. Summarized in Table 1 below are the mean concentrations in plasma of beagle dogs administered 30 mg./kg. doses orally of the 7-[D-$\alpha$-amino-$\alpha$-(p-hydroxyphenyl)acetamido]-3-(1,2,3-triazol-5-ylthiomethyl)-3-cephem-4-carboxylic acid propylene glycolate. Approximately 40 % of the dose was excreted in the urine within 8 hours of drug administration. The plasma half-life was about 1.36 hours.

Table 1

| | Plasma Concentration ($\mu$g/ml ± S.F.) |
|---|---|
| Time (hours) | 7-[D-$\alpha$-amino-$\alpha$-(p-hydroxyphenyl)-3-(1,2,3-triazol-5-ylthiomethyl)-3-cephem-4-carboxylic acid propylene glycolate |
| 0.08 | 0.04 ± — |
| 0.25 | 0.3 ± 0.1 |
| 0.50 | 5.9 ± 2.0 |
| 0.75 | 8.4 ± — |
| 1.0 | 15.8 ± 3.2 |
| 1.5 | 17.7 ± 2.0 |
| 2.0 | 18.7 ± 0.9 |
| 3.0 | 13.7 ± 1.2 |
| 4.0 | 8.4 ± 1.3 |
| 6.0 | 3.2 ± 0.4 |
| 8.0 | 1.6 ± 0.2 |

We claim:

1. A stable aqueous suspension useful for the treatment of bacterial infections in mammals comprising at least 30 mgm./ml. crystalline 7-[D-α-amino-α-(p-hydroxyphenyl)acetamido]-3-(1,2,3-triazol-5-ylthiomethyl)-3-cephem-4-carboxylic acid 1,2-propylene glycolate and having a pH in the range of 2.8 – 5.

2. A stable aqueous suspension of claim 1 wherein the 7-[D-α-amino-α-(p-hydroxyphenyl)acetamido]-3-(1,2,3-triazol-5-ylthiomethyl)-3-cephem-4-carboxylic acid 1,2-propylene glycolate has from 1.0 to 1.6 moles of 1,2-propylene glycol per mole of cephalosporin zwitterion.

3. A stable aqueous suspension of claim 2 wherein the 7-[D-α-amino-α-(p-hydroxyphenyl)acetamido]-3-(1,2,3-triazol-5-ylthiomethyl)-3-cephem-4-carboxylic acid 1,2-propylene glycolate is the crystalline monopropylene glycolate.

4. A stable aqueous suspension useful for the treatment of bacterial infections in mammals comprising at least 125 mgm./ml. of crystalline 7-[D-α-amino-α-(p-hydroxyphenyl)acetamido]-3-(1,2,3-triazol-5-ylthiomethyl)-3-cephem-4-carboxylic acid 1,2-propylene glycolate and having a pH in the range of 2.8 – 3.5.

5. A stable aqueous suspension of claim 4 wherein the 7-[D-α-amino-α-(p-hydroxyphenyl)acetamido]-3-(1,2,3-triazol-5-ylthiomethyl)-3-cephem-4-carboxylic acid 1,2-propylene glycolate has from 1.0 – 1.6 moles of 1,2-propylene glycol per mole of cephalosporin zwitterion.

6. A stable aqueous suspension of claim 5 wherein the 7-[D-α-amino-α(p-hydroxyphenyl)acetamido]-3-(1,2,3-triazol-5-ylthiomethyl)-3-cephem-4-carboxylic acid 1,2-propylene glycolate is the crystalline monopropylene glycolate.

* * * * *